United States Patent
Short

(10) Patent No.: US 8,118,023 B2
(45) Date of Patent: Feb. 21, 2012

(54) CPAP SYSTEM AND METHOD OF USE

(76) Inventor: Michael J. Short, Indianapolis, IN (US)

( * ) Notice: Subject to any disclaimer, the term of this patent is extended or adjusted under 35 U.S.C. 154(b) by 1049 days.

(21) Appl. No.: 12/008,066

(22) Filed: Jan. 9, 2008

(65) Prior Publication Data

US 2009/0173344 A1 Jul. 9, 2009

(51) Int. Cl.
*A61M 11/00* (2006.01)
(52) U.S. Cl. ............... 128/203.26; 128/204.18
(58) Field of Classification Search ........... 128/205.23, 128/204.17, 203.26, 203.27, 204.18, 204.21, 128/205.25
See application file for complete search history.

(56) References Cited

U.S. PATENT DOCUMENTS

| | | | |
|---|---|---|---|
| 4,806,768 A * | 2/1989 | Keutenedjian | 250/436 |
| 5,165,395 A * | 11/1992 | Ricci | 128/202.22 |
| 6,349,722 B1 * | 2/2002 | Gradon et al. | 128/203.17 |
| 6,470,888 B1 * | 10/2002 | Matter | 128/207.14 |
| 7,683,029 B2 * | 3/2010 | Hindle et al. | 514/5.9 |
| 7,814,907 B2 * | 10/2010 | Bremner et al. | 128/205.23 |
| 2002/0078733 A1 * | 6/2002 | Seakins et al. | 73/29.02 |
| 2006/0177356 A1 * | 8/2006 | Miller | 422/121 |
| 2007/0163588 A1 * | 7/2007 | Hebrank et al. | 128/204.18 |

\* cited by examiner

*Primary Examiner* — Steven Douglas
(74) *Attorney, Agent, or Firm* — Daniel J. O'Connor

(57) ABSTRACT

A system and method for treating obstructive sleep apnea (OSA) by means of a Continuous Positive Airway Pressure (CPAP) system in which is included an ultra-violet light source to remove bacteria and contaminants which may cause respiratory infection in a patient being treated. The ultraviolet light source is contained in a specially designed chamber comprising aluminum or equivalent suitable materials. The ultraviolet chamber is positioned directly downstream of a humidification unit and includes specially positioned baffles to protect connecting elements and other system components from any possible damage.

8 Claims, 4 Drawing Sheets

CPAP SYSTEM AND METHOD OF USE

BACKGROUND AND OBJECTS OF THE INVENTION

The present invention is generally related to the CPAP arts which stands for Continuous Positive Airway Pressure systems and methods of use. Such are utilized for the treatment of Obstructive Sleep Apnea (OSA).

CPAP devices have proven to be very successful in the effective treatment of OSA patients.

A typical CPAP device includes filters which are intended to reduce the risk of respiratory infection for OSA patients. A typical instruction manual for a CPAP system encourages regular filter change. If a humidifier is included in the system, water should be changed on a daily basis to prevent stagnation of the humidifying moisture.

Since a continuous positive air flow is supplied to the OSA patient, the patient becomes particularly susceptible to respiratory infections. Such are of course very serious matters so it becomes a critical matter to supply the cleanest air possible to the OSA patient.

Accordingly, it is an object of the present invention to set forth a CPAP system with improved air treatment to reduce the risk of respiratory infection for patients being treated for obstructive sleep apnea.

It is a further object to demonstrate an improved medical treatment method including an air purifying device which is economical to manufacture and which may be readily installed in existing CPAP systems.

It is a still further object to show an air treatment device having a specialized design and including, inter alia, an ultraviolet light source and baffle elements to confine the UV effects to a limited area.

These and other objects and advantages of the present invention will be apparent to those of skill in the art from the description which follows.

PRIOR ART PATENTS AND DESIGNS

During the course of preparing this specification for submission to the U.S. Patent and Trademark Office, a full search of the prior art was conducted.

U.S. Pat. No. 7,036,506 issued to McAuliffe et al on May 2, 2006 shows a CPAP device with a specialized flow diverter to enhance system performance.

U.S. Pat. No. 7,115,097 issued to Johnson on Oct. 3, 2006 teaches the use of a logic and alarm system to alert a patient or attending medical personnel. The Johnson patent includes reference to a humidification unit as part of the overall system.

The present invention includes a specialized air decontamination section of a type which is not shown in the prior art related to CPAP systems. Its critical utility is to reduce or eliminate the risk of respiratory infection for a patient undergoing treatment for obstructive sleep apnea (OSA).

SUMMARY OF THE INVENTION

A specially designed air treatment device is shown for use with a CPAP system in order to greatly reduce the risk of respiratory infection for patients being treated for sleep apnea.

Considering the benefit to patients health and well-being, it is expected that the design will be covered by routine insurance company funding.

The air treatment device comprises a container or chamber having a central ultraviolet light source which is utilized to treat contaminated air. Specially positioned baffles are used to direct air flow and to retain the UV light within a confined treatment area.

The air treatment device is comprised of aluminum and has a generally oval shape.

The invention also comprises specific method steps which are part of an overall treatment system for sleep apnea patients.

BRIEF DESCRIPTION OF THE DRAWING FIGURES

FULL DESCRIPTION OF THE PREFERRED EMBODIMENTS

Figure 1:
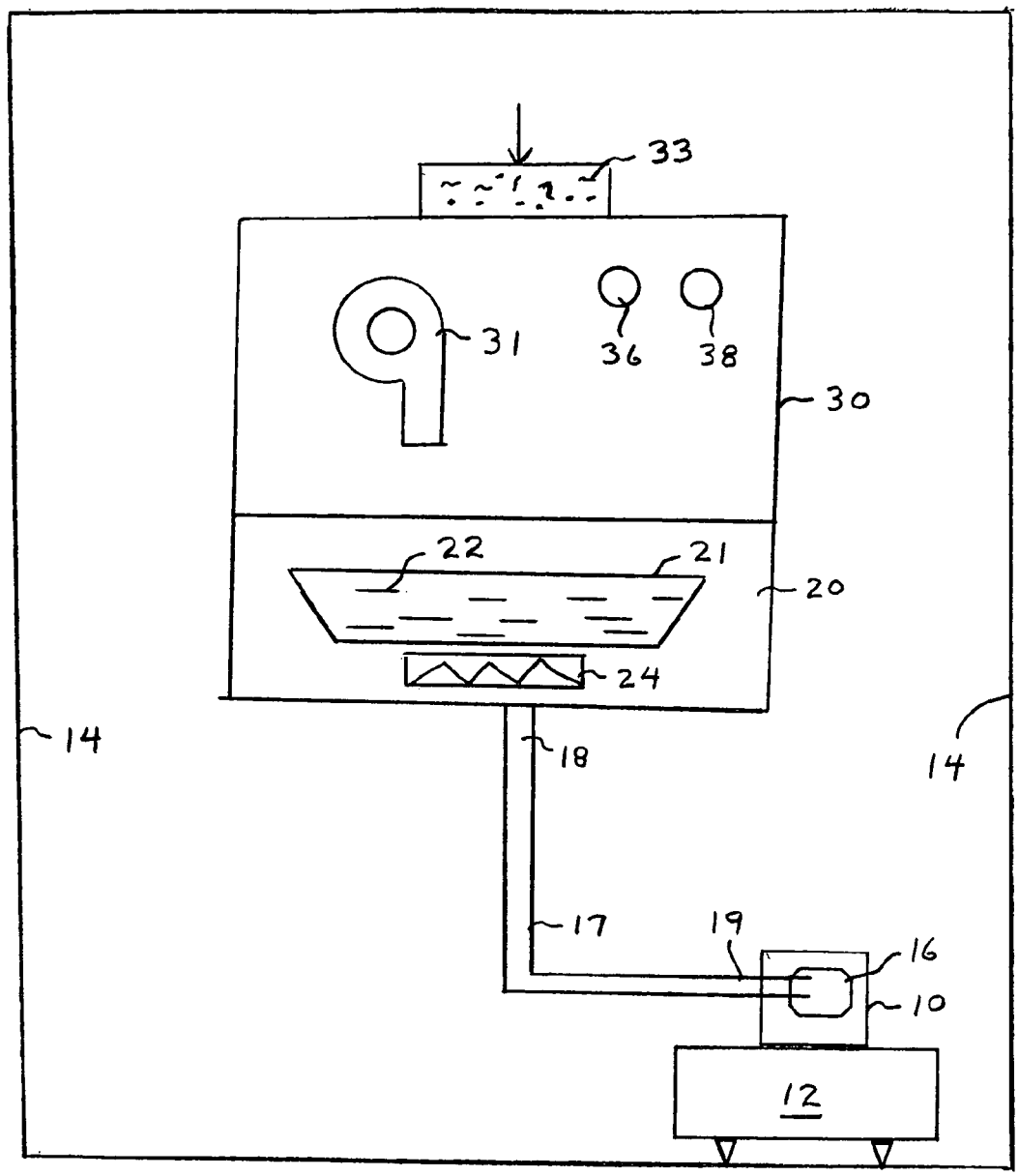
FIG. 1 is a schematic view of a continuous positive airway pressure (CPAP) system as used with a humidifier to supply air to a patient being treated for obstructive sleep apnea (OSA).
Figure 2:
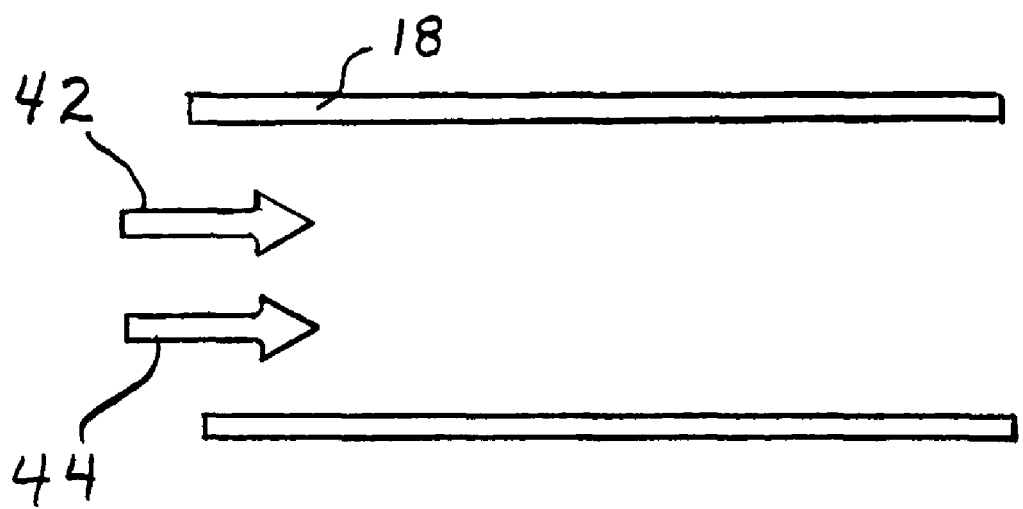
FIG. 2 is a schematic view of a typical air delivery tube and indicates possible sources of contamination which may be passed on to a patient.

Referring to the Prior Art drawings of FIGS. 1 and 2, a sleep apnea patient is indicated schematically at numeral 10 as on bed 12 in a surrounding room 14.

Patient 10 has a mask 16. A positive pressure air flow is supplied to the mask 16 by means of line 17. Line 17 has a right end 19 connected to the mask and a left end 18 connected to a combined CPAP and humidifier system.

The humidifier is indicated at numeral 20 and includes a water tray 21 with water 22 container therein. An electric heating element to vaporize water is shown schematically at numeral 24.

A Continuous Positive Airway Pressure (CPAP) device 30 is indicated as having a blower 31 as an essential part of the system. An air filter 33 is also schematically shown.

Speed control elements for the blower are indicated at numerals 36 and 38.

Various other CPAP system components and uses are shown in the cited prior art patents.

It is important to realize that obstructive sleep apnea patients are subject to a high risk of respiratory infection since the patient's airway is normally held in an open position via the CPAP positive air flow.

It is also critical to note that many CPAP systems are utilized in a residential room 14 as opposed to a professional treatment room which contains, hopefully, less contaminating bacteria which can cause a respiratory infection in the patient.

Especially in a residential room 14 setting, it is known that even the best filters 33 capture and remove only part of the contaminants. In residential uses, the CPAP system may be placed beside or even beneath a bed contributing further to contaminants supplied to a patient.

Thus, as indicated in FIG. 2, the air supplied to the tube 18 will contain significant contaminants 42 which come from residential room 14.

Another source of contamination for the sleep apnea patient is indicated at arrow 44. This represents bacteria or other contaminants arising from the water 22 contained within the tray of the humidifier.

It is known that water standing for only a few hours builds up significant bacteria-type particles. Especially in a residential setting, where the humidifier water may not be changed for days at a time, the water is a significant source of possibly infecting bacteria as indicated by arrow 44. Such contaminants thus proceed to the respiratory areas of the sleep apnea patient.

Although the CPAP systems contain warning instructions and warning labels regarding the danger of respiratory infection, if, for example, the filter devices are not regularly changed or the humidifier water is not properly replaced, it is known that such warnings are not effective to protect the patient.

Even if warnings are heeded, existing filters and poor water quality often result in a dangerous supply of air to the patient as indicated by arrows 42 and 44.

In order to help remedy the above-described bacteria problem, a container including an ultraviolet (UV) light is included in the system.

Figure 3:
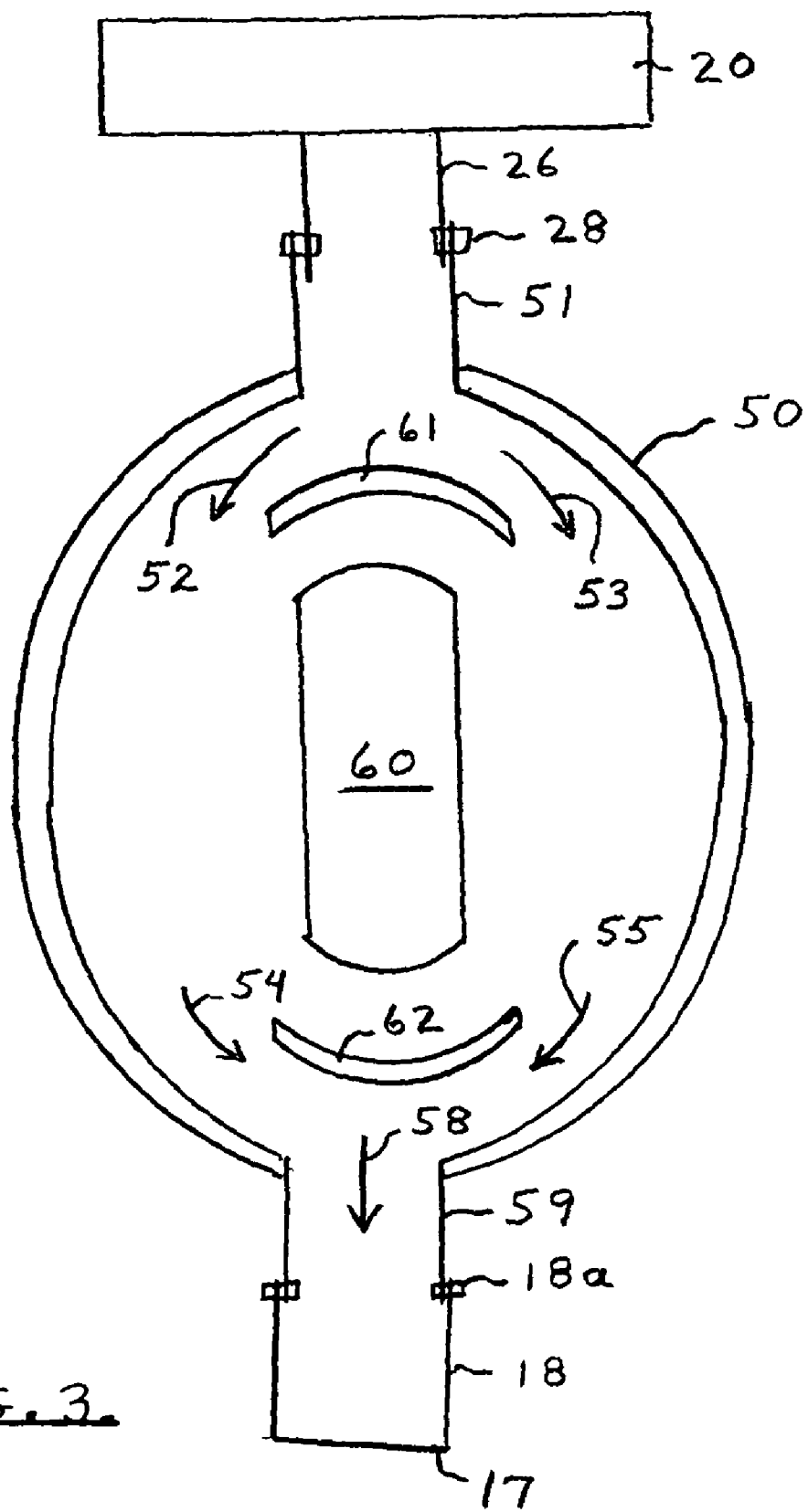
FIG. 3 is a schematic view of an air treatment device which is designed to be placed into a CPAP system to reduce the risk of respiratory infection for a treated patient.

Such UV light container is shown in FIG. 3.

The UV light container 50 has an upper entry port 51 which is connected to a lower flow port 26 of humidifier 20 by means of, for example, a rubber sleeve 28.

An ultraviolet light source 60 is shown as located in a central part of the container 50.

Also included are baffles 61 and 62 to be further described.

As indicated by the flow arrows 52 and 53, air flows around the upper baffle 61 and into the chamber and around the ultraviolet (UV) light 60.

The chamber 50 is only on the order of several inches wide so that air flow is in close proximity to the UV light 60.

As a result of the ultraviolet (UV) light treatment of air being supplied to a sleep apnea patient, most bacteria and contaminants are destroyed or rendered inactive.

As further shown by flow arrows 54 and 55, air flow moves around the lower baffle 62 and to the container exit port 59.

Exit port 59 is connected to the end 18 of supply tube 17 via suitable fastener means indicated schematically at numeral 18a.

The then-sanitized air flow 58 proceeds through the system to the patient supply tube 17 and ultimately to the patient as previously shown in FIG. 1.

It is noted that the container or chamber 50 is preferably fabricated of aluminum or other equivalent materials.

The container or chamber 50 is also preferably shaped as an oval to provide enhanced air flow there-through and efficient supply to the patient.

The upper and lower baffles 61 and 62 respectively are provided to block ultraviolet light rays from shining directly onto the other system components such as the plastic humidifier 20 or the plastic air supply tube 17.

Thus, other system components are protected from the UV rays and the ultraviolet light 60 only impacts on the air being treated.

The baffles 61 and 62 also direct air flow evenly through the chamber 50 so that an efficient air decontamination is effected.

The baffles 61 and 62 are curved downwardly and upwardly respectively as shown. Other equivalent light directing and UV light blocking shapes may be utilized.

Thus, for a relatively low cost, a system is created which greatly reduces the risk of infection for an obstructive sleep apnea patient.

Because of the enhanced patient benefits, it is anticipated that any added system or method costs would be covered by available health insurance funds.

Figure 4:
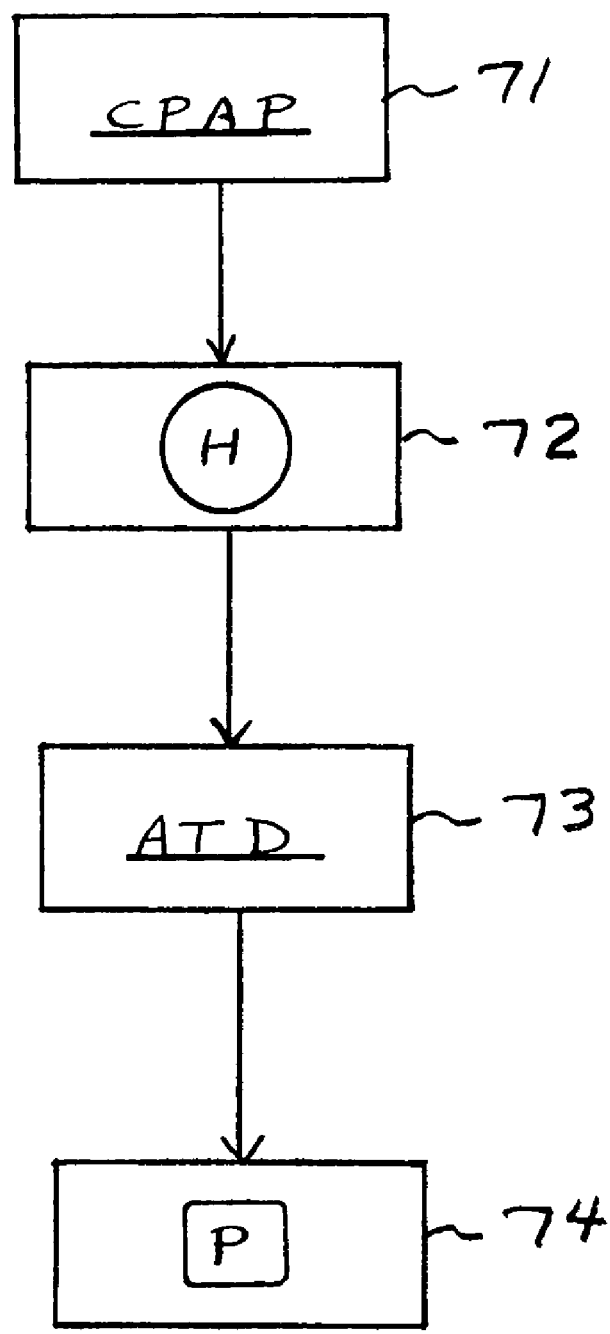
FIG. 4 is a block diagram of the method steps which comprise an important aspect of the medical treatment invention.

The method steps which form an important part of the invention are illustrated schematically in the block diagram of FIG. 4.

Blocks 71, 72, 73 and 74 broadly indicate the method steps which are as follows.

A) Provide a continuous positive airway pressure (CPAP) system which includes a blower and means for adjusting air flow to a patient being treated for obstructive sleep apnea (OSA).

B) Add a humidifier unit to the air flow path just downstream of the CPAP device, wherein the humidifier has a removable tray to facilitate regular addition and change of water.

C) Providing an air treatment device (ATD) which comprises an aluminum and generally oval-shaped chamber containing an ultraviolet (UV) light to destroy contaminants in the air. The ATD has specially designed baffle elements.

D) Supplying treated air to a patient being treated for obstructive sleep apnea (OSA) via an air flow line or hose and a mask.

While a particular system and method of use have been described and shown herein, it is intended in this specification to cover all equivalent systems and related methods of use. For example, the air treatment device (ATD) is intended for use with the various combined CPAP and humidifier systems in the sleep apnea treating arts. The ATD and associated baffles may be fabricated in various shapes and with various connector and support elements to achieve the desired air purifying results. The power supply to the ultraviolet light contained within the ATD may be preferably derived from the power supplied to the CPAP system. It is thus advantageous to place the ATD just downstream of the CPAP system.

The invention is further defined by the claims appended hereto.

I claim:

1. A treating method for obstructive sleep apnea patients comprising the steps of:
    a) providing a continuous positive airway pressure system including at least one air flow device and at least one filter element for purifying air,
    b) providing a humidifier including a water tray and heating element which are located downstream of said continuous positive airway pressure device,
    c) providing a contained section downstream of said humidifier, said contained section including an ultraviolet light source,
    d) providing that all of the air supplied to an OSA patient pass over said ultraviolet source to provide enhanced air purification,
    e) providing that said contained section for the ultraviolet light source includes at least one baffle element which protects system components from possible damage.

2. The treating method of claim 1 wherein said contained section comprises a chamber having an inlet port and an exit port, said inlet port being adjacent to the humidifier.

3. The treating method of claim 2 wherein the exit port of said chamber is connected to a hose which supplies air to a sleep apnea patient.

4. The treating method of claim 3 wherein the chamber is generally oval in shape to provide enhanced air flow and efficient reflection of rays from the ultraviolet light.

5. The treating method of claim 4 wherein the chamber is fabricated of aluminum.

6. The treating method of claim 5 wherein the chamber has a first upper baffle and a second lower baffle.

7. The treating method of claim 6 wherein the upper baffle is curved downwardly and the lower baffle is curved upwardly.

8. An air treatment chamber which removes bacteria and contaminants from air being supplied to a sleep apnea patient comprising:
- an inlet port adapted to be connected to an upstream humidifier device,
- an exit port adapted to be connected to a downstream hose which supplies air to a sleep apnea patient,
- a ultraviolet light source located in a central portion of said air treatment chamber,
- the air treatment chamber further including an upper baffle element and a lower baffle element,
- wherein the air treatment chamber is generally oval-shaped.

* * * * *